United States Patent [19]

Van Doorn et al.

[11] Patent Number: 4,794,165

[45] Date of Patent: Dec. 27, 1988

[54] CARBON MONOXIDE/OLEFIN POLYMERIZATION WITH BIDENTATE LIGAND CONTAINING

[75] Inventors: Johannes A. Van Doorn; Johannes J. M. Snel; Eit Drent, all of Cm Amsterdam, Netherlands

[73] Assignee: Shell Oil Company, Houston, Tex.

[21] Appl. No.: 135,426

[22] Filed: Dec. 21, 1987

[30] Foreign Application Priority Data

Feb. 23, 1987 [NL] Netherlands ................. 8700443

[51] Int. Cl.$^4$ ............................................. C08G 67/02
[52] U.S. Cl. ................................................ 528/392
[58] Field of Search ........................................ 528/392

[56] References Cited

U.S. PATENT DOCUMENTS

| | | | |
|---|---|---|---|
| 2,495,286 | 1/1950 | Brubaker | 260/63 |
| 3,694,412 | 9/1972 | Nozaki | 260/63 |
| 4,740,625 | 4/1988 | Drent | 528/392 |

FOREIGN PATENT DOCUMENTS

| | | |
|---|---|---|
| 0121965 | 10/1984 | European Pat. Off. . |
| 0181014 | 5/1986 | European Pat. Off. . |
| 0213671 | 3/1987 | European Pat. Off. . |
| 229408 | 7/1987 | European Pat. Off. . |
| 1081304 | 3/1965 | United Kingdom . |

Primary Examiner—Harold D. Anderson

[57] ABSTRACT

A process for the production of a linear alternating polymer of carbon monoxide and at least one ethylenically unsaturated hydrocarbon comprises contacting the carbon monoxide and hydrocarbon in the presence of a catalyst composition formed from a palladium compound, an anion of a non-hydrohalogenic acid having a pKa below about 4 and a phosphino-arsinoalkane bidentate ligand.

7 Claims, No Drawings

CARBON MONOXIDE/OLEFIN POLYMERIZATION WITH BIDENTATE LIGAND CONTAINING

FIELD OF THE INVENTION

This invention relates to an improved method of producing linear alternating polymers of carbon monoxide and at least one ethylenically unsaturated hydrocarbon. More particularly, the invention relates to an improved process for the production of polyketone polymers which employs a mixed phosphorus-arsenic bidentate ligand.

BACKGROUND OF THE INVENTION

The class of polymers of carbon monoxide and olefin(s) has been known for a number of years. Brubaker, U.S. Pat. No. 2,495,286 produced such polymers in the presence of free radical catalysts, i.e., peroxy compounds. U.K. No. 1,081,304 produced similar polymers of higher carbon monoxide content in the presence of alkylphosphine complexes of palladium salts as catalyst. Nozaki extended this process through the use of arylphosphine complexes of palladium salts and certain inert solvents, e.g., U.S. Pat. No. 3,694,412.

More recently the class of linear alternating polymers of carbon monoxide and at least one ethylenically unsaturated hydrocarbon, e.g., ethylene or ethylene and propylene, has become of greater interest, in part because of the greater availability of these polymers. The polymers have been shown to be of the formula —CO(A)— where A is the moiety of the unsaturated hydrocarbon polymerized through the ethylenic unsaturation. For example, when the ethylenically unsaturated hydrocarbon is ethylene, the polymer is represented by the formula —CO(—CH$_2$—CH$_2$—)—. The general process for the production of such polymers is illustrated by a number of published European Patent Applications including No. 0,121,965 and No. 0,181,014. The process generally involves a catalyst composition formed from a compound of the Group VIII metals palladium, cobalt or nickel, the anion of a non-hydrohalogenic acid having a pKa below 2 and a bidentate ligand of phosphorus, arsenic or antimony.

The bidentate ligands are generally of the formula

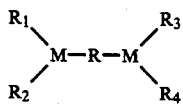

wherein R$_1$, R$_2$, R$_3$, R$_4$ and R are organic groups and M independently is a member of Group VA of the Periodic Table of Elements selected from phosphorus, arsenic and antimony. The process of polymer production is operable with ligands containing a variety of combinations of M atoms, which combinations may call for the two M atoms to be the same or alternatively to be different. Although general preference is given to bidentate ligands of the above formula wherein both M atoms are phosphorus, it has been found than when "mixed" bidentate ligands are employed, i.e., a ligand of differing M atoms is used, one particular combination of M atoms provided results which are improved over other combinations of mixed M atoms and even improved over combinations where both M atoms are the same but are other than phosphorus.

SUMMARY OF THE INVENTION

This invention relates to an improved method of producing linear alternating polymers of carbon monoxide and at least one ethylenically unsaturated hydrocarbon in the presence of a catalyst composition formed from a palladium compound, the anion of certain non-hydrohalogenic acids and a bidentate ligand containing two different Group VA atoms. More particularly, the invention relates to such an improved process wherein the bidentate ligand is a phosphino-arsino-alkane bidentate ligand.

DESCRIPTION OF THE INVENTION

The process of the invention is a process for the production of a polymer of carbon monoxide and at least one ethylenically unsaturated hydrocarbon in the presence of a catalyst composition formed from a palladium compound, the anion of certain non-hydrohalogenic acids and a bidentate ligand comprising an alkane substituted by a defined phosphino substituent and a defined arsino substituent.

The palladium compound is preferably a palladium salt of a monocarboxylic acid of up to 10 carbon atoms such as palladium hexanoate, palladium octanoate and palladium decanoate. Preferably, however, the palladium compound is the salt of a lower alkanoic acid of up to 4 carbon atoms such as palladium acetate, palladium propionate and palladium butyrate. Best results are obtained when the palladium compound is palladium acetate.

The anion component is the anion of a non-hydrohalogenic acid having a pKa of less than about 4 (measured in aqueous solution at 18° C.). Illustrative of these anions are the anions of mineral acids such as perchloric acid, sulfuric acid, phosphoric acid and nitrous acid or anions of organic acids including sulfonic acids such as p-toluenesulfonic acid, 2-hydroxypropane-2-sulfonic acid, methanesulfonic acid and trifluoromethanesulfonic acid as well as carboxylic acids such as trifluoroacetic acid, trichloroacetic acid, dichloroacetic acid, difluoroacetic acid, tartaric acid and 2,5-dihydroxybenzoic acid. The anion is preferably the anion of a non-hydrohalogenic acid having a pKa less than about 2 and in particular the anion of trifluoroacetic acid or p-toluenesulfonic acid.

The anion is typically employed in an amount from about 0.5 equivalents per gram atom of palladium (as the compound) to about 200 equivalents per gram atom of palladium. Preferably, the anion is employed in an amount from abut 1 equivalent to about 100 equivalents per gram atom of palladium.

The anion is most frequently provided in the form of the free acid but in an alternate modification the anion is provided as a metal salt, particularly as the salt of a transition metal which is not a member of Group VIII of the Periodic Table of Elements, e.g., as a copper salt. In yet another modification, the anion and the palladium compound are provided as a single compound such as palladium p-toluenesulfonate.

The bidentate ligand of the invention is a phosphino-arsino alkane represented by the formula

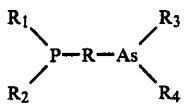

wherein $R_1$, $R_2$, $R_3$, and $R_4$ independently are aryl groups of up to 10 carbon atoms which are hydrocarbyl or are alkoxyhydrocarbyl and R is a divalent hydrocarbyl bridging group of up to 10 carbon atoms with from 2 to 4 carbon atoms inclusive in the bridge joining the arsenic and the phosphorus. Preferred are the ligands wherein the groups $R_1$, $R_2$, $R_3$ and $R_4$ are the same and are phenyl or alkoxyphenyl, particularly phenyl or those alkoxyphenyl groups where at least one alkoxy group is ortho to the phosphorus or arsenic. Illustrative of such preferred groups are phenyl, 2-methoxyphenyl, 2,4-dimethoxyphenyl and 2-ethoxyphenyl. Best results are obtained when each of $R_1$, $R_2$, $R_3$ and $R_4$ is phenyl. The preferred R groups have from 2 to 4 carbon atoms inclusive, each of which is in the phosphorus-arsenic bridge. Particularly preferred are the dimethylene and trimethylene groups, i.e. the —$CH_2CH_2$— and —$CH_2$—$CH_2$—$CH_2$— groups.

Illustrative of suitable bidentate ligands are 1-(diphenylphosphino)-3-(diphenylarsino)propane, 1-(diphenylphosphino)-2-(diphenylarsino)ethane, 1-[di(2-methoxyphenyl)phosphino]-3-[di(2-methoxyphenyl)arsino]-propane and 1-(diphenylphosphino)-4-[di(2,4-diethoxyphenyl)arsino]-butane. The bidentate ligand is employed in an amount from about 0.1 mol per mol of palladium compound to about 3 mol per mol of palladium compound, preferably in an amount from about 0.75 mol to about 2 mol per mol of palladium compound.

In order to enhance the activity of the catalyst composition it is useful on occasion to employ a quinone as a catalyst modifier. Suitable quinones are hydrocarbyl quinones of up to 15 carbon atoms and include benzoquinones, naphthaquinones and anthraquinones. Preferred quinones are benzoquinones, particularly 1,4-benzoquinones. No quinone catalyst modifier is required, but when a quinone is employed a quantity of quinone up to 10,000 mol of quinone per gram atom of palladium compound is satisfactory with an amount of quinone up to about 5,000 mol per gram atom of palladium compound being preferred.

The polymers of the invention are linear alternating polymers of carbon monoxide and at least one ethylenically unsaturated hydrocarbon. Suitable ethylenically unsaturated hydrocarbons useful as precursors of the polyketones have from 2 to 20 carbon atoms inclusive, preferably up to 10 carbon atoms, and are aliphatic such as ethylene and other α-olefins including propylene, 1-butene, 1-octene and 1-docecene, or are arylaliphatic containing an aryl substituent on an otherwise aliphatic molecule, particularly an aryl substituent on a carbon of the ethylenic unsaturation. Illustrative of this latter class of ethylenically unsaturated hydrocarbons are styrene, p-methylstyrene, p-ethylstyrene and m-methylstyrene. Preferred polyketone polymers are copolymers of carbon monoxide and ethylene or terpolymers of carbon monoxide and ethylene and a second α-olefin of at least 3 carbon atoms, particularly propylene.

The structure of the preferred polymers is that of a linear alternating polymer of carbon monoxide and ethylenically unsaturated hydrocarbon and the polymer will contain substantially one molecule of carbon monoxide for each molecule of the hydrocarbon. When terpolymers of carbon monoxide, ethylene and a second ethylenically unsaturated hydrocarbon, i.e., a hydrocarbon of at least 3 carbon atoms, are produced there will be at least 2 units incorporating a moiety of ethylene per unit incorporating a moiety of the second hydrocarbon, preferably from about 10 to about 100 units incorporating a moiety of ethylene per unit incorporating a moiety of the second hydrocarbon. The polymer chain is therefore illustrated by the formula

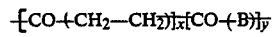

where B is the moiety obtained by polymerization of the second ethylenically unsaturated hydrocarbon through the ethylenic unsaturation. The —CO—(—$CH_2$—$CH_2$—)— units and the —CO—(—B—)— units are formed randomly throughout the polymer chain and the ratio of y:x is no more than about 0.5. In the modification of the invention which produces copolymers of carbon monoxide and ethylene without the presence of a second hydrocarbon, the polymers are represented by the above formula wherein y=0. When y is other than 0, i.e., terpolymers are produced. Ratios of y:x from about 0.01 to about 0.1 are preferred. The end groups or "caps" of the polymer chain will depend upon what materials are present during the production of the polymer and whether and how the polymer has been purified. The precise nature of the end groups is of little significance with regard to the overall properties of the polymer so that the polymer is fairly represented in terms of the polymer chain as depicted above.

Of particular interest are the polymers of molecular weight from about 1,000 to about 200,000, particularly those of molecular weight from about 10,000 to about 50,000 containing substantially equimolar quantities of carbon monoxide and unsaturated hydrocarbon. The physical properties of such polyketone polymers depend in part on the molecular weight of the polymer, whether the polymer is a copolymer or a terpolymer and the relative proportion of any second hydrocarbon present in the case of a terpolymer. Typical melting points of such polymers are from about 175° C. to about 300° C. and more frequently from about 210° C. to about 270° C.

Polymerization is suitably conducted in the gaseous phase but more typically is conducted in the liquid phase in the presence of an inert diluent, particularly a lower alkanol such as methanol or ethanol. The amount of catalyst composition to be employed is a catalytic quantity, typically an amount sufficient to provide from abut $1 \times 10^{-7}$ gram atom of palladium to about $1 \times 10^{-3}$ gram atom of palladium per mol of ethylenically unsaturated hydrocarbon to be polymerized. Preferred amounts of catalyst are from about $1 \times 10^{-6}$ to about $1 \times 10^{-4}$ gram atom of palladium per mol of hydrocarbon to be polymerized. The molar ratio of ethylenically unsaturated hydrocarbon to carbon monoxide will suitably be from about 10:1 to about 1:5, particularly from about 5:1 to about 1:2.

The carbon monoxide, unsaturated hydrocarbon and catalyst are contacted under polymerization conditions. Typical reaction temperatures are from about 20° C. to about 200° C., preferably from about 30° C. to about 150° C. Reaction pressures are from about 1 bar to about 200 bar, more often from about 20 bar to about 100 bar. The method of contacting is not critical and is conducted by shaking, stirring or other conventional means. Subsequent to reaction, the polymer product is recovered as by filtration or decantation. The polymer will, on occasion, contain residues of the catalyst which are removed, if desired, by contacting with a solvent which is selective for the residues.

The polyketone polymers are known materials of known properties. The polyketones are premium thermoplastics having utility in the production of shaped articles for the food and drink industry and for shaped parts for automotive purposes. The polyketone polymers are drawn into wires or made into cables or are extruded into beams and other structural parts of sue in the construction industry.

The invention is further illustrated by the following Comparative Experiment (not of the invention) and Illustrative Embodiments which should not be construed as limiting. Each of the copolymers produced was found to have a melting point of 257° C. and was shown by $^{13}$C-NMR to have a linear alternating structure of the formula —CO—(—CH$_2$—CH$_2$—)—.

Illustrative Embodiment I

The compound 1-(diphenylphosphino)-3-(diphenylarsino)propane was produced by the following procedure. To 300 ml of liquid ammonia in a mechanically stirred reaction vessel maintained at —78° C. were consecutively added 2 g of sodium and 13.1 g of triphenylarsine. After one hour, 2.3 g of ammonium chloride was added and after an additional 30 minutes a solution of 11.3 g of 1-(diphenylphosphino)-3-chloropropane in 100 ml of dry tetrahydrofuran was added. The reaction mixture was stirred for an additional 12 hours while the temperature was allowed to rise to ambient temperature. Ethyl acetate and water were added to the reaction mixture and the organic layer was separated and dried over magnesium sulfate. The drying agent was removed by filtration and the solvent was removed by evaporation. The crude 1-(diphenylphosphino)-3-(diphenylarsino)propane was purified by recrystallization from ethanol.

Comparative Experiment I

The compound 1-(diphenylphosphino)-3-(diphenylstibino)propane was produced by the procedure of Illustrative Embodiment I except that 15.2 g of triphenylstibine was added instead of 13.1 g of triphenylarsine.

Comparative Experiment II

A carbon monoxide/ethylene copolymer was produced by charging a mechanically stirred autoclave of 100 ml capacity with a catalyst solution comprising 20 ml of methanol, 0.05 mmol of palladium acetate, 0.075 mmol of trifluoroacetic acid and 0.06 mmol of 1,3-bis(-diphenylarsino)propane.

The air present in the autoclave was removed by evacuation and ethylene was added until a pressure of 15 bar was reached followed by carbon monoxide until a pressure of 30 bar was reached. The reaction mixture was heated to 80° C. and maintained at that temperature for one hour. The polymerization reaction was then terminated by cooling to room temperature and releasing the pressure. The copolymer was recovered by filtration, washed with methanol and dried in vacuo at room temperature. The yield of copolymer was 2.3 g.

Illustrative Embodiment II

A copolymer of carbon monoxide and ethylene was produced by the procedure of Comparative Experiment II except that 0.06 mmol of 1-(diphenylphosphino)-3-diphenylarsino)propane was used instead of the 1,3-bis(-diphenylarsino)propane and the reaction time was 1.5 hr instead of 1 hr. The yield of copolymer was 3.3 g.

Comparative Experiment III

A copolymer of carbon monoxide and ethylene was produced by the procedure of Comparative Experiment II except that the catalyst solution contained 0.06 mmol of 1-(diphenylphosphino)-3-diphenylstibino)propane instead of the 1,3-bis(diphenylarsino)propane and the reaction time was 1.5 hr instead of 1 hr. The yield of copolymer was 0.2 g.

Illustrative Embodiment III

A copolymer of carbon monoxide and ethylene was produced by charging to a mechanically stirred autoclave of 300 ml capacity a catalyst solution comprising 50 ml of methanol, 0.1 mmol of palladium acetate, 2 mmol of p-toluenesulfonic acid and 0.15 mmol of 1-(diphenylphosphino)-3-(diphenylarsino)ethane. The air present in the autoclave was removed by evacuation and ethylene was added until a pressure of 20 bar was reached followed by carbon monoxide until a pressure of 50 ml was reached. The reaction mixture was heated to 80° C. and maintained for 5 hours when reaction was terminated by cooling to room temperature and releasing the pressure. The copolymer product was removed by filtration, washed with methanol and dried in vacuo at room temperature. The yield of copolymer was 3.5 g.

Illustrative Embodiment IV

If a polymer of carbon monoxide, ethylene and propylene is produced by the procedure of Illustrative Embodiment III except that propylene is additionally present in the reaction mixture, a linear alternating terpolymer of carbon monoxide, ethylene and propylene will be produced in good yield.

What is claimed is:

1. In the process of producing a linear alternating polymer of carbon monoxide and at least one ethylenically unsaturated hydrocarbon in the presence of a catalyst composition formed from a palladium compound, the anion of a non-hydrohalogenic acid having a pKa below about 4 and a bidentate ligand incorporating two atoms of Group VA elements, the improvement which comprises employing a ligand wherein one of said Group VA atoms is phosphorus and the other Group VA atom is arsenic.

2. The process of claim 1 wherein the ligand is represented by the formula

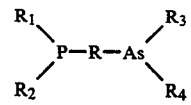

wherein R$_1$, R$_2$, R$_3$, and R$_4$ independently are aryl groups of up to 10 carbon atoms, R is a divalent hydrocarbon bridging group of up to 10 carbon atoms and from 2 to 4 carbon atoms inclusive in the bridge joining the arsenic and the phosphorus.

3. The process of claim 2 wherein the groups R$_1$, R$_2$, R$_3$ and R$_4$ are the same and are selected from phenyl or alkoxyphenyl and R is —CH$_2$—CH$_2$—CH$_2$—.

4. The process of claim 3 wherein each of R$_1$, R$_2$, R$_3$ and R$_4$ is phenyl.

5. In the process of producing a linear alternating copolymer of carbon monoxide and ethylene in the presence of a catalyst composition formed from a palladium salt of a monocarboxylic acid of up to 10 carbon atoms, the anion of an acid selected from trifluoroacetic acid or p-toluenesulfonic acid and a bidentate ligand of the formula

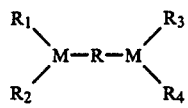

wherein $R_1$, $R_2$, $R_3$, $R_4$ and R independently are organo groups and M independently is a Group VA atom, the improvement which comprises employing a bidentate ligand of the formula

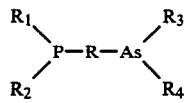

wherein $R_1$, $R_2$, $R_3$, and $R_4$ independently are aryl groups of up to 10 carbon atoms and R is dimethylene or trimethylene.

6. The process of claim 5 wherein $R_1$, $R_2$, $R_3$ and $R_4$ are the same and are selected from phenyl or alkoxyphenyl.

7. The process of claim 6 wherein $R_1$, $R_2$, $R_3$ and $R_4$ are phenyl and R is trimethylene.

* * * * *